(12) United States Patent
Nord et al.

(10) Patent No.: US 10,441,814 B2
(45) Date of Patent: Oct. 15, 2019

(54) METHOD AND APPARATUS TO EMPLOY A MULTI-LAYER MULTI-LEAF COLLIMATOR WHEN ADMINISTERING A RADIATION THERAPY TREATMENT

(71) Applicants: Varian Medical Systems, Inc., Palo Alto, CA (US); Varian Medical Systems International AG, Cham (CH)

(72) Inventors: Janne I. Nord, Espoo (FI); Jarkko Y. Peltola, Tuusela (FI); Esa Kuusela, Espoo (FI); Steven W. Prince, San Francisco, CA (US)

(73) Assignee: Varian Medical Systems International AG, Steinhausen (CH)

( * ) Notice: Subject to any disclaimer, the term of this patent is extended or adjusted under 35 U.S.C. 154(b) by 1071 days.

(21) Appl. No.: 14/865,890

(22) Filed: Sep. 25, 2015

(65) Prior Publication Data

US 2017/0087387 A1  Mar. 30, 2017

(51) Int. Cl.
*A61N 5/10* (2006.01)
*G21K 1/04* (2006.01)

(52) U.S. Cl.
CPC ......... *A61N 5/1045* (2013.01); *A61N 5/1036* (2013.01); *G21K 1/046* (2013.01);
(Continued)

(58) Field of Classification Search
CPC .. A61N 5/1036; A61N 5/1045; A61N 5/1047; A61N 5/1042; A61N 5/1065; A61N 5/1067; A61N 2005/1087; A61N 2005/1088; A61N 2005/1089; A61N 2005/109; G21K 1/046
See application file for complete search history.

(56) References Cited

U.S. PATENT DOCUMENTS 5,748,703 A   5/1998  Cosman
6,600,810 B1  7/2003  Hughes
(Continued)

OTHER PUBLICATIONS

Extended European Search Report for European Patent Application No. 16187121.5 dated Feb. 1, 2017; 7 pages.
(Continued)

*Primary Examiner* — Carrie R Dorna
(74) *Attorney, Agent, or Firm* — Fitch, Even, Tabin & Flannery LLP (57) ABSTRACT

A control circuit administers a radiation treatment plan that specifies a planned total radiation dose for a radiation treatment session for a given patient by modulating a radiation beam with at least one high-resolution aperture that is formed using one of a plurality of linearly-sequential high-resolution aperture possibilities. By one approach the foregoing comprises modulating the radiation beam using at least substantially only high-resolution apertures that are formed using a plurality of the linearly-sequential high-resolution aperture possibilities. In some cases the foregoing can comprise administering the radiation treatment plan using at least two separate radiation exposures for only a single treatment field, in which case, by one approach, each of the separate radiation exposures for the single treatment field can comprise modulating the radiation beam using at least substantially only high-resolution apertures.

13 Claims, 6 Drawing Sheets

(52) U.S. Cl.
CPC ............... *A61N 2005/1074* (2013.01); *A61N 2005/1095* (2013.01)

(56) References Cited

U.S. PATENT DOCUMENTS

| | | |
|---|---|---|
| 2001/0043669 A1 | 11/2001 | Ein-Gal |
| 2003/0026384 A1* | 2/2003 | Hernandez-Guerra .................... A61N 5/1042 378/65 |
| 2004/0184578 A1* | 9/2004 | Nakano .................. A61N 5/103 378/65 |
| 2012/0043482 A1 | 2/2012 | Prince et al. |

OTHER PUBLICATIONS

Article 94(3) EPC from European Patent Application No. 16187121.5 dated Feb. 21, 2018; 4 pages.

* cited by examiner

FIG. 10B

METHOD AND APPARATUS TO EMPLOY A MULTI-LAYER MULTI-LEAF COLLIMATOR WHEN ADMINISTERING A RADIATION THERAPY TREATMENT

RELATED APPLICATION(S)

This application is related to co-pending and co-owned U.S. patent application Ser. No. 14/865,863, entitled METHOD AND APPARATUS FOR USING A MULTI-LAYER MULTI-LEAF COLLIMATION SYSTEM and filed on even date herewith, which is incorporated by reference in its entirety herein.

TECHNICAL FIELD

These teachings relate generally to the administration of therapeutic doses of radiation and more particularly to the use of multi-leaf collimators.

BACKGROUND

Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and that can selectively move towards and away from one another via controlled motors. A typical multi-leaf collimator has many such pairs of leaves, often upwards of twenty, fifty, or even one hundred such pairs.

By passing a therapeutic radiation beam through the aperture(s) of a multi-leaf collimator the radiation beam can be modulated to better match the dosing requirements of the treatment session. These dosing requirements typically include (or at least presume) prescribing which body tissues to irradiate and which body tissues to avoid irradiating.

While a typical multi-leaf collimator represents an enormous improvement in terms of better shaping a radiation beam to meet such requirements, it nevertheless remains true that, at least some of the time, the resultant beam shape does not perfectly meet such requirements. This shortcoming typically arises as a function of the maximum resolution by which the multi-leaf collimator is able to shape the beam. When the leaves of the multi-leaf collimator have a cross-dimension of, for example, 1.0 centimeter, that is generally orthogonal to the incoming beam, that dimension imposes a corresponding limit as to the resolution capabilities of the collimator.

BRIEF DESCRIPTION OF THE DRAWINGS

The above needs are at least partially met through provision of the method and apparatus to employ a multi-layer multi-leaf collimator when administering a radiation therapy treatment described in the following detailed description, particularly when studied in conjunction with the drawings, wherein:

FIG. 10 (FIGS. 10A and 10B) comprises front-elevational views as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit administers a radiation treatment plan that specifies a planned total radiation dose for a radiation treatment session for a given patient by modulating a radiation beam with at least one high-resolution aperture that is formed using one of a plurality of linearly-sequential high-resolution aperture possibilities. By one approach the foregoing comprises modulating the radiation beam using at least substantially only high-resolution apertures that are formed using a plurality of the linearly-sequential high-resolution aperture possibilities. In some cases the foregoing can comprise administering the radiation treatment plan using at least two separate radiation exposures for only a single treatment field, in which case, by one approach, each of the separate radiation exposures for the single treatment field can comprise modulating the radiation beam using at least substantially only high-resolution apertures.

By one approach at least some of the plurality of linearly-sequential high-resolution aperture possibilities have a height resolution that is twice the resolution of aperture possibilities that are available with either a proximal or distal layer of a plurality of collimation leaf pairs alone. For many application settings it will be useful that at least substantially all of the plurality of linearly-sequential high-resolution aperture possibilities have a height resolution that is twice the resolution of aperture possibilities that are available with either of the proximal or distal layer of the plurality of collimation leaf pairs alone. In many cases such a high-resolution aperture has at least one boundary defined only by the proximal layer and at least one other boundary defined only by the distal layer.

These teachings are highly flexible in practice and will accommodate a variety of approaches in the foregoing regards. By one approach, for example, administering the radiation treatment plan comprises using two (and only two) separate exposures for a single treatment field and where the high-resolution apertures are grouped in sequential pairs and the sequential pairs of high-resolution apertures are separated from one another by a pair of sequential unused high-resolution aperture possibilities.

By another approach, and as another example in these regards, administering the radiation treatment plan comprises using three (and only three) separate exposures for a single treatment field and where the high-resolution apertures are each separated from a next sequential high-resolution aperture by a pair of sequential unused high-resolution aperture possibilities.

So configured, these approaches help address the deficiencies of prior art techniques that do not work well with two or more layers of multi-leaf collimators. In particular, the present teachings can greatly aid in leveraging such additional layers to improve the definition and/or resolution of beam-shaping apertures. Such improvements, in turn, can further help to assure that treatment targets receive a desired radiation dosage while non-targeted surrounding areas receive less unwanted radiation.

Figure 1:
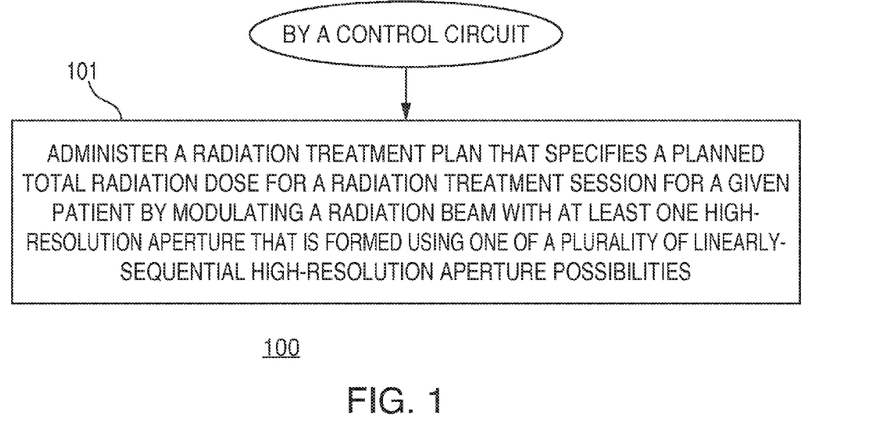
FIG. 1 comprises a flow diagram as configured in accordance with various embodiments of these teachings.
Figure 2:
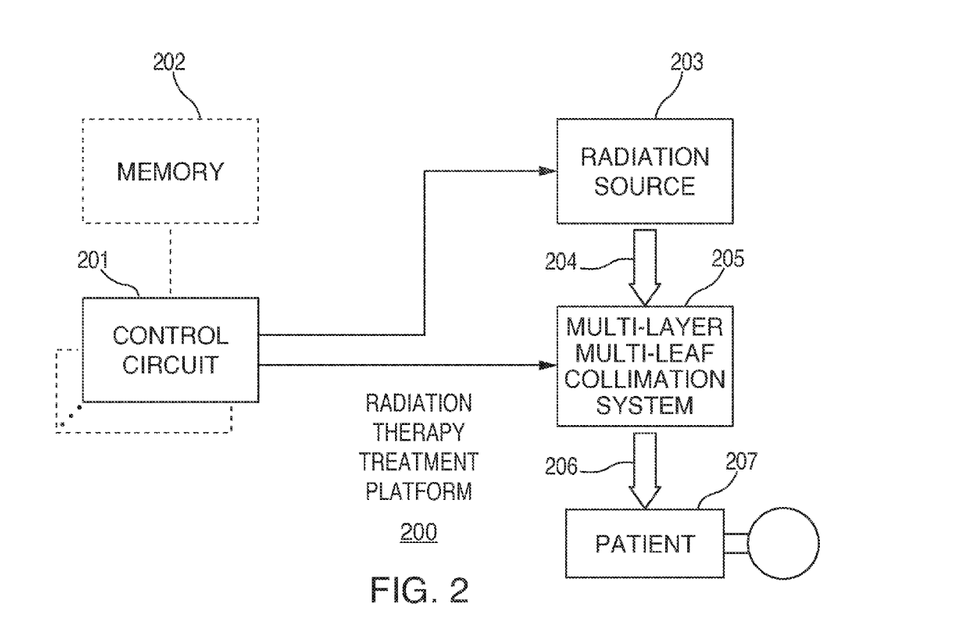
FIG. 2 comprises a block diagram as configured in accordance with various embodiments of these teachings.

These and other benefits may become clearer upon making a thorough review and study of the following detailed description. Referring now to the drawings, and in particular to FIG. 1, an illustrative process 100 that is compatible with many of these teachings will now be presented. For the sake of an illustrative example it is presumed here in that a control circuit of choice carries out the steps, actions, and/or functionality of this process 100. FIG. 2 presents an illustrative example in this regard.

As shown in FIG. 2, a radiation therapy treatment platform 200 can include or otherwise operably couple to a control circuit 201. Being a "circuit," the control circuit 201 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 201 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 201 is configured (for example, by using corresponding programming as will be well understood by those skilled in the art) to carry out one or more of the steps, actions, and/or functions described herein. It will also be understood that a "control circuit" can comprise multiple such components or platforms as well as suggested by the phantom control circuit box in FIG. 2.

By one optional approach the control circuit 201 operably couples to a memory 202. This memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

In addition to radiation treatment plans this memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The radiation therapy treatment platform 200 also includes a radiation source 203 that operably couples and responds to the control circuit 201. So configured, the corresponding radiation beam 204 as emitted by the radiation source 203 can be selectively switched on and off by the control circuit 201. These teachings will also accommodate having the control circuit 201 control the relative strength of the radiation beam 204. Radiation sources are well understood in the art and require no further description here.

The radiation beam 204 is directed towards a multi-layer multi-leaf collimation system 205 that also operably couples to the control circuit 201 to thereby permit the control circuit 201 to control movement of the collimation systems leaves and hence the formation and distribution of one or more radiation-modulating apertures. The resultant modulated radiation beam 206 then reaches a treatment target in a corresponding patient 207.

Figure 3:
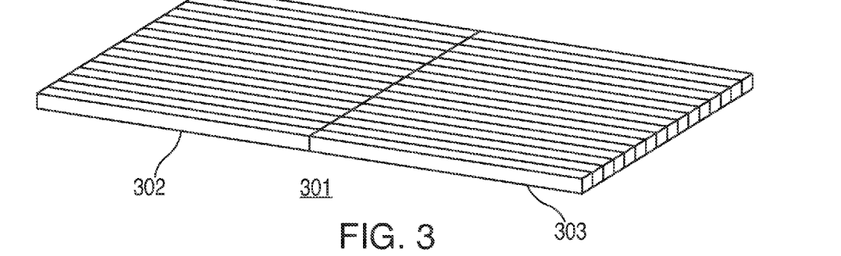
FIG. 3 comprises a perspective schematic view as configured in accordance with various embodiments of these teachings.

FIG. 3 presents a representative view of a first layer 301 of collimating leaves for the multi-layer multi-leaf collimating system 205. Generally speaking this first layer 301 includes a plurality of selectively movable collimating leaves 302 that each comprise a first leaf for a corresponding pair of collimating leaves. This first layer 301 also includes a second plurality of selectively movable collimating leaves 303 that each comprise a second leaf for the aforementioned pair of collimating leaves. So configured, when one or both collimating leaves as comprise a pair of collimating leaves are selectively moved away from one another, a beam-shaping aperture forms therebetween. (The manner by which electric motors can be employed to effect such movement comprises a well understood area of prior art endeavor. Accordingly, for the sake of brevity, additional details in those regards are not provided here.)

The second layer of collimating leaves for the multi-layer multi-leaf collimating system 205 can be identical to the first layer 301 described above. Or, if desired, these teachings will accommodate a variety of relatively small changes. For example, the second layer of collimating leaves may include one or more additional pairs of collimating leaves or one or more fewer pairs of collimating leaves as compared to the first layer 301. As another example, the collimating leaves of the second layer may be somewhat greater in width or somewhat lesser in width than the collimating leaves of the first layer 301.

Figure 4:
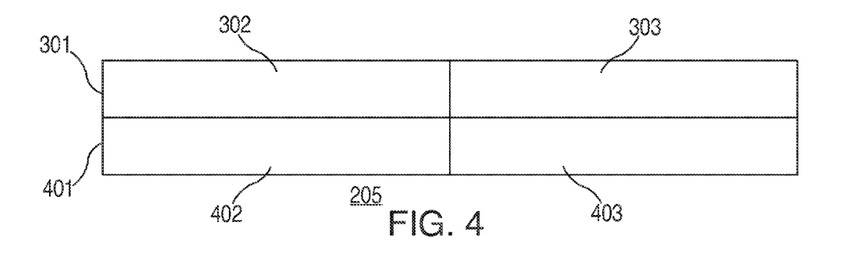
FIG. 4 comprises a front elevational schematic view as configured in accordance with various embodiments of these teachings.

In any event, and as generally represented in FIG. 4, the first layer 301 and second layer 401 of the collimating leaves are generally juxtaposed one atop the other (with or without some amount of intervening space as desired). In this example the first layer 301 comprises a so-called proximal layer and hence is oriented towards the aforementioned radiation source 203. Accordingly, the second layer 401 comprises a so-called distal layer that is oriented opposite the radiation source 203 and towards the patient 207.

In this illustrative example the collimating leaves of the first layer 301 are generally laterally aligned with the collimating leaves of the second layer 401. For example, the left side (as illustrated) collimating leaves 302 for the first layer 301 are laterally aligned with the left side collimating leaves 402 of the second layer 401. Similarly, the right side (as illustrated) collimating leaves 303 of the first layer 301 are laterally aligned with the right side collimating leaves 403 of the second layer 401. These teachings are highly flexible in practice and will accommodate other orientations and juxtapositions as may be useful to address the needs of a specific application setting. For example, it may be useful in some cases to laterally offset the collimating leaves of one layer from the collimating leaves of the other layer.

Figure 5:
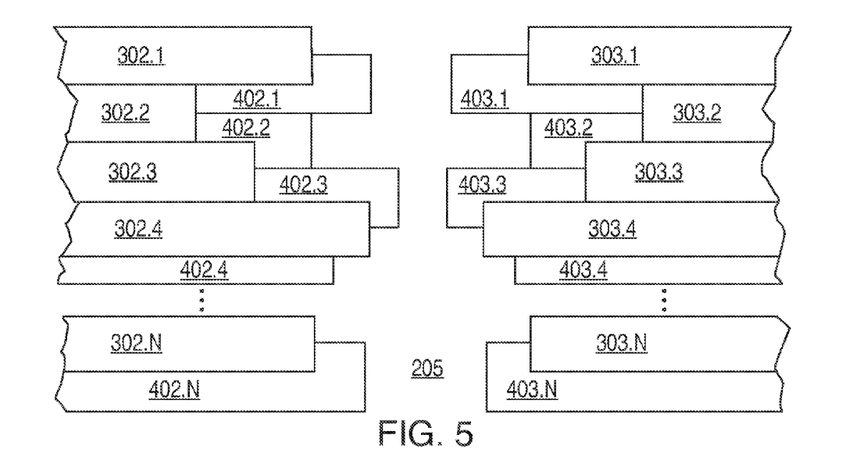
FIG. 5 comprises a top plan view as configured in accordance with various embodiments of these teachings.

Although the collimating leaves for these two layers 301 and 401 may be laterally aligned, as shown in FIG. 5 the collimation leaves for these two layers 301 and 401 are vertically offset with respect to one another. (It will be understood that the word "vertically" as used herein refers to the orientation context shown in these illustrations. In an application setting the multi-layer multi-leaf collimation system 205 can be oriented in any of a variety of ways. Accordingly, it will be further understood that the word "vertically" as used herein refers to the relative context of the collimation leaves when the multi-layer multi-leaf collimation system 205 itself is oriented vertically and upright which will not necessarily correlate to the orientation of the system in a particular application setting.)

Accordingly, it can be seen that the left-side collimating leaves 302.1-302.N (where "N" is an integer) of the first layer 301 each only partially overlap the left-side collimating leaves 402.1-402.N of the second layer 401. Similarly, the right-side collimating leaves 303.1-303.N of the first layer 301 each only partially overlap the right-side collimating leaves 403.1-403.N of the second layer 401. In the illustrated example the collimating leaves of each layer are offset vertically by fifty percent and accordingly the first layer 301 has collimating leaves that each overlap corresponding leaves of the second layer 401 by fifty percent as well. In this example the various leaves are depicted with the leaves of each leaf pair having been opened to some greater or lesser extent to facilitate better viewing of the collimating leaves of the second layer 401.

Figure 6:
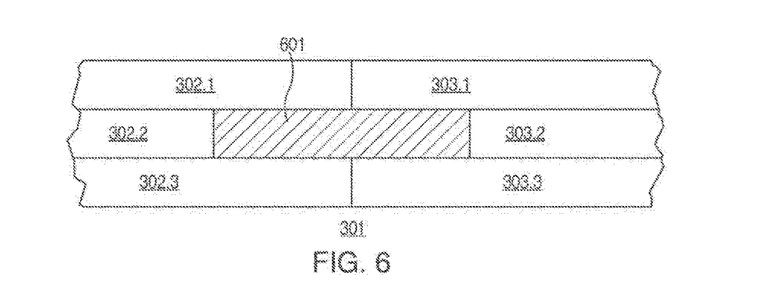
FIG. 6 comprises a top plan view as configured in accordance with various embodiments of these teachings.
Figure 7:
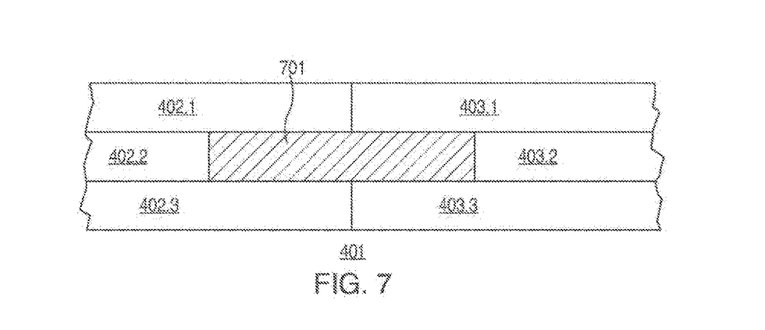
FIG. 7 comprises a top plan view as configured in accordance with various embodiments of the invention.
Figure 8:
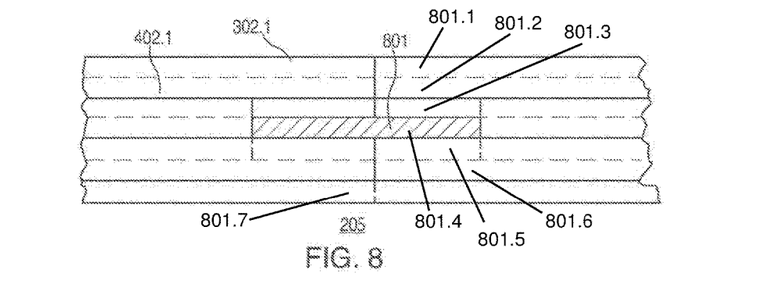
FIG. 8 comprises a top plan view as configured in accordance with various embodiments of these teachings.

The applicant has determined that the aperture resolution capable of a multi-leaf collimator can be significantly increased by employing such a multi-layer multi-leaf collimator 205. FIGS. 6-8 provide an illustrative example in these regards. FIG. 6 depicts an aperture 601 formed using collimating leaves of the first layer 301. In this simple example, a pair of collimating leaves 302.2 and 303.2 have been moved away from one another while the collimating leaves above and below that pair of collimating leaves remain closed to form that aperture 601. Necessarily, this aperture 601 has a vertical dimension identical to the vertical dimensions of that pair of collimating leaves.

FIG. 7 presents an aperture 701 formed in an identical manner to that just described, albeit using collimating leaves of the second layer 401. Again, the resultant aperture 701 has a vertical dimension that is necessarily identical to the vertical dimensions of the collimating leaves.

FIG. 8 illustrates the aperture 801 that results when the two layers 301 and 401 are stacked one atop the other in a vertically offset manner as described above. Accordingly, the two apertures 601 and 701 described above only partially overlap one another to form this resultant aperture 801. In this particular illustrative example the aperture 801 has a vertical dimension that is only one half the vertical dimension of the collimating leaves. Accordingly, this particular approach yields a 2X improvement in aperture resolution in these regards. That improvement in resolution provides an opportunity to more precisely shape a radiation beam 204 to match the contours of a given treatment target.

Accordingly, such an aperture 801 is referred to herein as a high-resolution aperture as such an aperture has higher resolution than apertures that can normally be formed by leaf pairs of either layer 301 or 401 alone. And, as is also illustrated in FIG. 8, such a configuration gives rise to a plurality of linearly-sequential high-resolution aperture possibilities (numbered here as 801.1 through 801.7), it being understood that there are approximately twice as many linearly-sequential high-resolution aperture possibilities as there are leaf pairs in either layer 301 or 401.

The word "possibility" serves to indicate that a high-resolution aperture can be formed in the space indicated if desired through ordinary and usual manipulation of the aforementioned leaf pairs. In the illustration of FIG. 8, while there are seven such linearly-sequential high-resolution aperture possibilities, only one possibility (the one denoted by reference numeral 801.4) actually features a realized high-resolution aperture 801.

Generally speaking, at least most of these high-resolution apertures will have at least one boundary (typically a horizontal boundary when presuming the orientation of convenience shown in the drawings) that is defined only by the proximal layer 301 and at least one other boundary (typically opposite the aforementioned boundary) that is defined by only the distal layer 401.

In many application settings it will be useful if at least some of the plurality of linearly-sequential high-resolution aperture possibilities have a height resolution that is twice the resolution of aperture possibilities that are available with either of the proximal or distal layer of the plurality of leaf pairs alone, and in many cases it will be useful if at least substantially all of those possibilities have such a height resolution. (As used herein, this reference to "substantially all" shall be understood to mean at least ninety percent of all such possibilities.)

With continued reference to the foregoing illustrations, and in particular to FIGS. 1 and 2, this process 100 can be used in conjunction with a radiation therapy treatment platform 200 as described above having a multi-layer multi-leave collimation system 205 wherein a proximal layer 301 of a plurality of collimation leaf pairs 302 and 303 are vertically offset with respect to a distal layer 401 of a plurality of collimation leaf pairs 402 and 403 to form a plurality of linearly-sequential high-resolution aperture possibilities. At block 101 this process 100 provides for having the control circuit 201 administer a radiation treatment plan that specifies a planned total radiation dose for a radiation treatment session for a given patient 207 by modulating a radiation beam 204 with at least one high-resolution aperture that is formed using one of the plurality of linearly-sequential high-resolution aperture possibilities.

Because the high-resolution apertures are formed using overlapping low-resolution apertures, it will not necessarily be possible to form a high-resolution aperture for each and every available high-resolution aperture possibility. Instead, and as will be described in more detail below, it will sometimes be appropriate or even necessary to space one or more high-resolution apertures apart from one another with intervening unused high-resolution aperture possibilities. As a result, these teachings will accommodate using two or more separate radiation exposures for only a single treatment field in order to permit each of the separate radiation exposures for the single treatment field to comprise modulating the radiation beam using only (or at least substantially only) high-resolution apertures.

Figure 9:
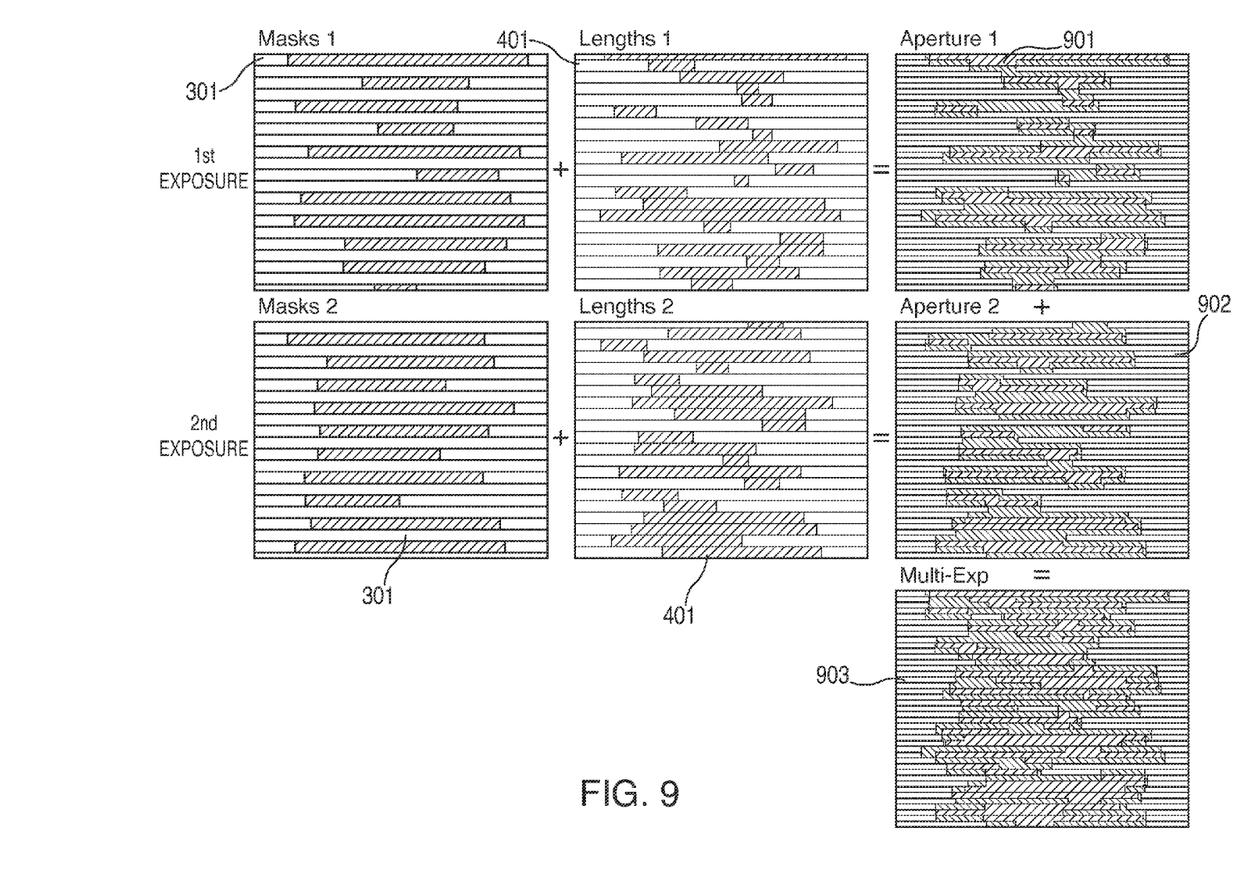
FIG. 9 comprises front-elevational views as configured in accordance with various embodiments of these teachings.

FIG. 9 provides one illustrative example in these regards. In this example a first set 901 of high-resolution apertures are employed during a first exposure of radiation for a particular treatment field followed by a second set 902 of high-resolution apertures that are employed during a second exposure of radiation for that same treatment field. In both the first set 901 and the second set 902 the high-resolution apertures are grouped in sequential pairs with each such pair of high-resolution apertures being separated from any next-adjacent pairs of high-resolution apertures by a pair of sequential unused high-resolution aperture possibilities.

The net aggregated effect of this two-exposure approach that employs such a grouping and spacing is illustrated at reference numeral 903 where, in this example, each and every high-resolution aperture possibility features a corresponding high-resolution aperture. Accordingly, by using, in this case, only high-resolution apertures the radiation beam can be more precisely modulated and the radiation dose accordingly more carefully administered.

FIG. 9 also illustrates the low-resolution apertures that are formed using the proximal layer 301 and the distal layer 401 of the multi-layer multi-leaf collimation system 205 which, when combined one with the other in an offset manner as described above, yields the corresponding high-resolution apertures shown at the right in the drawing. In this particular example a low-resolution aperture is formed using only every other leaf pair in the proximal layer 301 for both exposures. (The counter-cross-hatched areas in the two sets 901 and 902 of the high-resolution apertures represent an area where a low-resolution aperture formed in one layer does not coincide with a low-resolution aperture formed in the other layer.)

Figures 10, 10A:
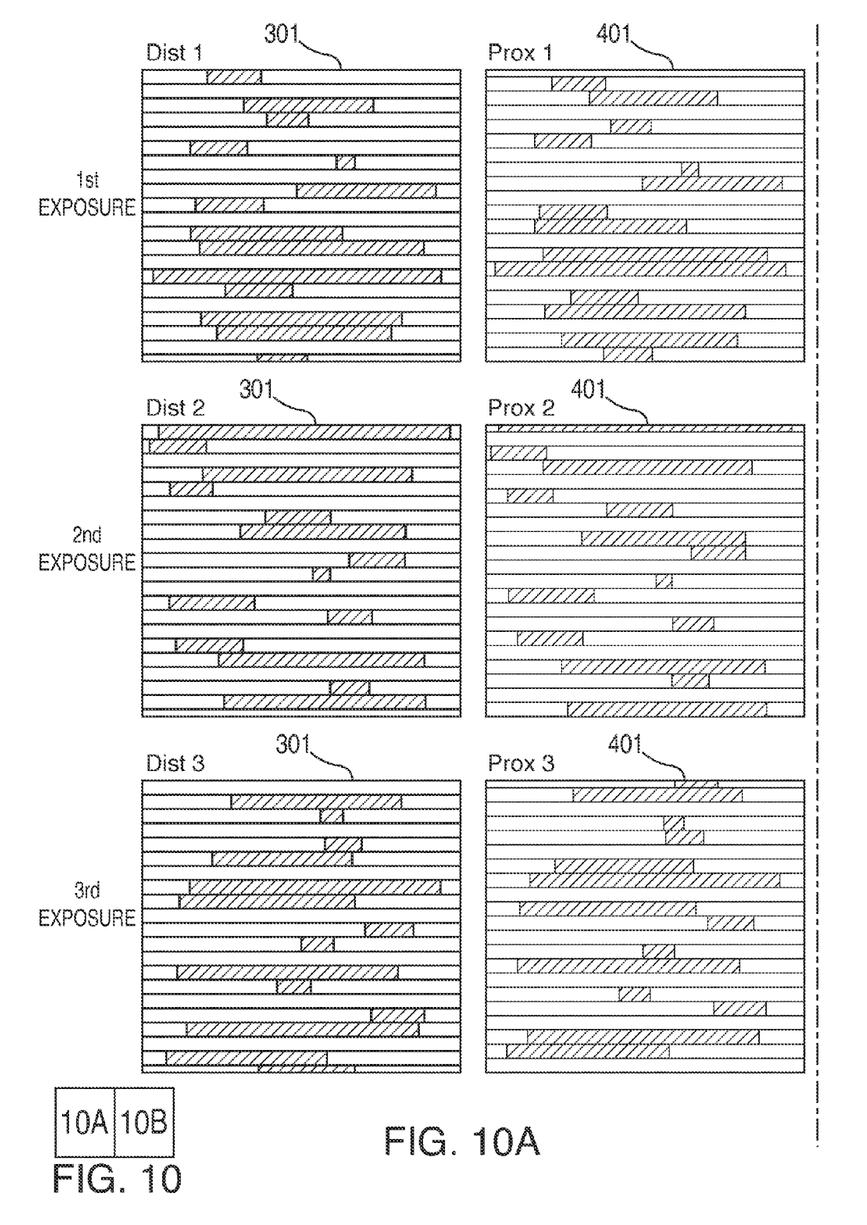
Figure 10B:
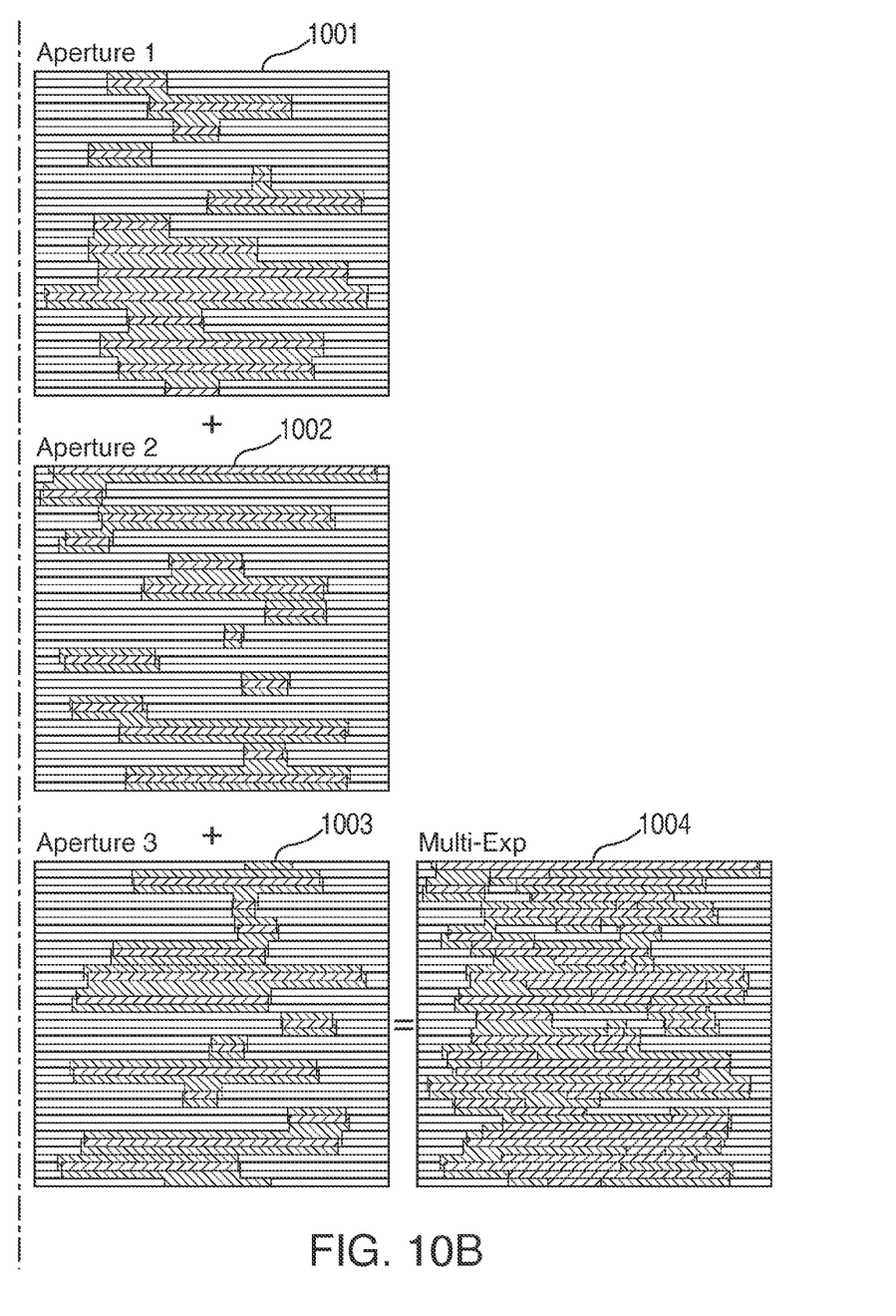

FIG. 10 provides another illustrative example in these regards. In this example a first set 1001 of high-resolution apertures are employed during a first exposure of radiation for a particular treatment field followed by a second set 1002 and then a third set 1003 of high-resolution apertures that are employed during a second and third exposure of radiation for that same treatment field. In all three sets 1001, 1002, and 1003 the high-resolution apertures are each separated from any next-adjacent high-resolution apertures by a sequential pair of unused high-resolution aperture possibilities.

The net effect of this three-exposure approach that employs such a grouping and spacing is illustrated at reference numeral 1004 where, in this example, each and every high-resolution aperture possibility again features a corresponding high-resolution aperture. It may be noted that the result shown at reference numeral 1004 is essentially the same as that depicted at reference numeral 903 in FIG. 9 discussed above. Accordingly, these two examples constitute two different multi-exposure approaches to achieving a same net, aggregate pattern of high-resolution apertures.

FIG. 10 also again illustrates the low-resolution apertures that are formed using the proximal layer 301 and the distal layer 401 of the multi-layer multi-leaf collimation system 205 which, when combined one with the other in an offset manner as described above, yields the corresponding high-resolution apertures shown at the right in the drawing. The counter-cross-hatched areas in the three sets 1001, 1002, and 1003 of the high-resolution apertures also again represent an area where a low-resolution aperture formed in one layer does not coincide with a low-resolution aperture formed in the other layer.

So configured, a multi-layer multi-leaf collimation system can be successfully employed in a way that permits using only low-resolution apertures to nevertheless ultimately form in combination with one another only (or substantially only) high-resolution apertures to thereby help assure a more precise and accurate dosing of a patient's treatment target.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method for use with a radiation therapy treatment platform having a multi-layer multi-leaf collimation system wherein a proximal layer of a plurality of collimation leaf pairs are vertically offset with respect to a distal layer of a plurality of collimation leaf pairs such that the two multi-layer multi-leaf collimators combine to form a plurality of linearly-sequential high-resolution aperture possibilities, the method comprising:

by a control circuit:
administering a radiation treatment plan that specifies a planned total radiation dose for a radiation treatment session for a given patient by, at least in part and for a first treatment field, administering two and only two radiation exposures, wherein:
a first radiation exposure for the first treatment field comprises modulating a radiation beam using a first fixed aperture that includes at least one high-resolution aperture that is formed using one of the plurality of linearly-sequential high-resolution aperture possibilities; and
a second separate radiation exposure for the first treatment field comprises modulating the radiation beam using a second fixed aperture that is different from the first fixed aperture and that includes at least one high-resolution aperture that is formed using one of the plurality of linearly-sequential high-resolution aperture possibilities.

2. The method of claim 1 wherein at least some of the plurality of linearly-sequential high-resolution aperture possibilities have a height resolution that is twice the resolution of aperture possibilities that are available with either of the proximal or distal layer of the plurality of collimation leaf pairs alone.

3. The method of claim 2 wherein at least substantially all of the plurality of linearly-sequential high-resolution aperture possibilities have a height resolution that is twice the resolution of aperture possibilities that are available with either of the proximal or distal layer of the plurality of collimation leaf pairs alone.

4. The method of claim 1 wherein at least one of the high-resolution apertures has at least one boundary defined only by the proximal layer and at least one other boundary defined only by the distal layer.

5. The method of claim 1 wherein the first radiation exposure for the first treatment field comprises modulating a radiation beam using a first fixed aperture comprised of at least substantially only high-resolution apertures that are formed using the plurality of linearly-sequential high-resolution aperture possibilities and wherein the second radiation exposure for the first treatment field comprises modulating a radiation beam using a second fixed aperture that is different from the first fixed aperture and that is comprised of at least substantially only high-resolution apertures that are formed using the plurality of linearly-sequential high-resolution aperture possibilities.

6. The method of claim 1 wherein the high-resolution apertures are grouped in sequential pairs and the sequential pairs of high-resolution apertures are separated from one another by a pair of sequential unused high-resolution aperture possibilities of the plurality of linearly-sequential high-resolution aperture possibilities.

7. An apparatus comprising:
a source of therapeutic radiation configured to emit a radiation beam;
a multi-layer multi-leaf collimation system wherein a proximal layer of a plurality of collimation leaf pairs are vertically offset with respect to a distal layer of a plurality of collimation leaf pairs such that the two multi-layer multi-leaf collimators combine to form a plurality of linearly-sequential high-resolution aperture possibilities; and
a control circuit operably coupled to the source of therapeutic radiation and to the multi-layer multi-leaf collimation system, the control circuit being configured to administer a radiation treatment plan that specifies a planned total radiation dose for a radiation treatment session for a given patient, at least in part and for a first treatment field, by administering two and only two radiation exposures, wherein:
a first radiation exposure for the first treatment field comprises modulating a radiation beam using a first fixed aperture that includes at least one high-resolution aperture that is formed using one of the plurality of linearly-sequential high-resolution aperture possibilities; and
a second separate radiation exposure for the first treatment field comprises modulating the radiation beam using a second fixed aperture that is different from the first fixed aperture and that includes at least one high-resolution aperture that is formed using one of the plurality of linearly-sequential high-resolution aperture possibilities.

8. The apparatus of claim 7 wherein at least some of the plurality of linearly-sequential high-resolution aperture possibilities have a height resolution that is twice the resolution of aperture possibilities that are available with either of the proximal or distal layer of the plurality of collimation leaf pairs alone.

9. The apparatus of claim 8 wherein at least substantially all of the plurality of linearly-sequential high-resolution aperture possibilities have a height resolution that is twice the resolution of aperture possibilities that are available with either of the proximal or distal layer of the plurality of collimation leaf pairs alone.

10. The apparatus of claim 7 wherein at least one of the high-resolution apertures has at least one boundary defined only by the proximal layer and at least one other boundary defined only by the distal layer.

11. The apparatus of claim 7 wherein the control circuit is configured to administer the radiation treatment plan by modulating the radiation beam using at least substantially only high-resolution apertures that are formed using the plurality of the linearly-sequential high-resolution aperture possibilities.

12. The apparatus of claim 7 wherein the high-resolution apertures are grouped in sequential pairs and the sequential pairs of high-resolution apertures are separated from one another by a pair of sequential unused high-resolution aperture possibilities of the plurality of linearly-sequential high-resolution aperture possibilities.

13. A method for use with a radiation therapy treatment platform having a multi-layer multi-leaf collimation system wherein a proximal layer of a plurality of collimation leaf pairs are vertically offset with respect to a distal layer of a plurality of collimation leaf pairs such that the two multi-layer multi-leaf collimators combine to form a plurality of linearly-sequential high-resolution aperture possibilities, the method comprising:
by a control circuit:
administering a radiation treatment plan that specifies a planned total radiation dose for a radiation treatment session for a given patient by, at least in part and for a first treatment field, administering two radiation exposures, wherein:
a first radiation exposure for the first treatment field comprises modulating a radiation beam using a first fixed aperture that includes at least one high-resolution aperture that is formed using one of the plurality of linearly-sequential high-resolution aperture possibilities; and
a second separate radiation exposure for the first treatment field comprises modulating the radiation beam using a second fixed aperture that is different from the first fixed aperture and that includes at least one high-resolution aperture that is formed using one of the plurality of linearly-sequential high-resolution aperture possibilities.

* * * * *

UNITED STATES PATENT AND TRADEMARK OFFICE
CERTIFICATE OF CORRECTION

PATENT NO. : 10,441,814 B2  
APPLICATION NO. : 14/865890  
DATED : October 15, 2019  
INVENTOR(S) : Janne I. Nord et al.

Page 1 of 1

It is certified that error appears in the above-identified patent and that said Letters Patent is hereby corrected as shown below:

On the Title Page

Column 1, in (72) Inventors, delete "Tuusela" and insert --Tuusula--.

Column 1, in (73) Assignee, insert --Varian Medical Systems, Inc., Palo Alto, CA (US)-- above Varian Medical Systems International AG, Steinhausen (CH).

Signed and Sealed this  
Twenty-fourth Day of December, 2019

Andrei Iancu  
*Director of the United States Patent and Trademark Office*